(12) United States Patent
Gen et al.

(10) Patent No.: US 6,534,562 B2
(45) Date of Patent: Mar. 18, 2003

(54) TOUGH DENTURE AND METHOD FOR PRODUCING THE SAME

(75) Inventors: Shokyu Gen, Kyoto (JP); Sadami Tsutsumi, Kyoto (JP); Toshio Kita, Kyoto (JP)

(73) Assignee: BMG Inc., Kyoto (JP)

( * ) Notice: Subject to any disclaimer, the term of this patent is extended or adjusted under 35 U.S.C. 154(b) by 0 days.

(21) Appl. No.: 09/812,623

(22) Filed: Mar. 20, 2001

(65) Prior Publication Data

US 2001/0034380 A1 Oct. 25, 2001

(30) Foreign Application Priority Data

Mar. 22, 2000 (JP) .......................................... 2000-126660

(51) Int. Cl.[7] ........................ A61C 13/087; A61K 6/083; C08L 31/02
(52) U.S. Cl. ........................ 523/115; 523/120; 524/533; 433/34; 433/48
(58) Field of Search ................................ 523/115, 116, 523/120; 524/533, 81, 264; 433/34, 36, 39

(56) References Cited

U.S. PATENT DOCUMENTS 5,182,332 A * 1/1993 Yamamato et al. ......... 525/305
5,561,208 A * 10/1996 Takahashi et al. .......... 526/281
5,665,795 A * 9/1997 Koushima et al. .......... 523/223
6,133,343 A * 10/2000 Hatanaka .................... 523/201
6,136,886 A * 10/2000 Deguchi ..................... 523/116

OTHER PUBLICATIONS

USM Polymer Science Online Laboratory Directory, Department of Polymer Sci., U. of Southern Mississippi, www.psrc.usm.edu 1998.*

* cited by examiner

Primary Examiner—Tae H. Yoon
(74) Attorney, Agent, or Firm—Jordan and Hamburg LLP

(57) ABSTRACT

The present invention provides a tough denture and a method for producing the denture, which includes solid PMMA as a main component, being added to polar elastomer selected from a group of polyacrylate rubber copolymer, methylmethacrylate-alkylacrylate-styrene terpolymer, and fluororubber, and is fabricated in a process of being mixed and injected into a denture mold. A PMMA denture of present invention shows improved safety to living organisms and increased productivity of molding because of excellent mechanical properties and remarkable elution volume decrease after polymerization in comparison with ordinary type dentures of heat-polymerized PMMA. Furthermore, it is possible to widely apply the denture clinically because of good adaptability in oral applications with economical advantages.

9 Claims, No Drawings

TOUGH DENTURE AND METHOD FOR PRODUCING THE SAME

BACKGROUND OF THE INVENTION

1. Field of the Invention

The present invention relates to a tough denture fabricated of injectable polymethyl-methacrylate (PMMA) and a method for producing the same. The denture in this invention includes a portion of or a whole artificial tooth, and an artificial tooth base.

2. Description of the Related Art

Present dentures employed clinically, which are known are heat-polymerized type PMMA, injection-type polysulfone (PS) and polycarbonate (PC) resins. The heat-polymerized type PMMA is fabricated of a mixture of methyl-methacrylate (MMA) monomer liquid and PMMA prepolymer powder by mixing and heat-polymerizing in a denture-shaped mold. However, there are several product drawbacks in this method, namely, unstable shape caused by high shrinkage of polymer during polymerization, poor mechanical properties such as impact resistance and toxicity to a living organism that is pointed out to cause an allergy by dissolving a lot of monomer residue after polymerization.

Because of the above drawbacks, PS and PC are employed as injectable denture materials instead of the heat-polymerized type PMMA. However, PS shows poor impact resistance and PC shows toxicity and environmental pollution of bis-phenol A remaining as monomer residue, and poor adhesion to mending material of PMMA that is difficult to improve.

Although it is desirous in the dental field to invent and apply a novel denture that shows excellent mechanical properties including impact resistance and has little monomer residue, however there is still not a PUMA denture which meets the above conditions.

An object of the invention is to provide an excellent denture fabricated of PMMA and a method for the production thereof, having little monomer residue including the bis-phenol A, dissolved in one's mouth, and showing excellent mechanical properties including impact resistance.

SUMMARY OF THE INVENTION

The present invention provides a tough denture and a method for the production thereof, which comprises solid PMMA as a main component, being added to polar elastomer selected from the group of polyacrylate rubber copolymer, methylmethacrylate-alkylacrylate-styrene terpolymer, and fluororubber, and is fabricated in a process of being mixed and injected into a denture mold.

The term "toughness" in the present denture means that tensile and Izod impact strengths are more than 75.0 MPa and 1.62 kg·cm/cm$^2$, and bending strain at 5.0 kgf is less than 3.00 mm. Furthermore, elution volume from monomer residue after PMMA polymerization is less than 3% in the invented denture.

DETAILED DESCRIPTION OF THE INVENTION

PMMA of the present invention which is possibly employed is not only pure syndiotactic PMMA used in general industry, but also a blend of syndiotactic and atactic PMMAs in order to improve mechanical and thermal properties by forming a stereo complex.

The higher the tacticity of the PMMA blend composed of both syndiotactic and atactic PMMAs, the better. The tacticity is preferably more than 60%, more preferably more than 80%. The blend ratio of both PMMAs is preferable in a range of 40–60% to 60–40% in order to form a stereo complex, in spite of the fact that the ratio is freely changed. A weight-average molecular weight of PMMA for the invented denture, in both phases, is preferably in a range of 100 to 300 thousand, more preferably in a range of 120 to 250 thousand. A PMMA denture having the weight-average molecular weight of less than 100 thousand shows poor mechanical properties in spite of the fact that it easily injects. Therefore, PMMA having a weight-average molecular weight of more than 100 thousand is preferable.

Although PMMA of a high weight-average molecular weight is preferable in view of mechanical properties, however a uniform-shaped denture is difficult to fabricate from PMMA having a weight-average molecular weight of more than 300 thousand, because it shows poor fluid properties and is therefore poor for injecting as a result of high melt viscosity.

PMMA of present invention is added to polar elastomer selected from a group of polyacrylate rubber copolymer, methylmethacrylate-alkylacrylate-styrene terpolymer, and fluororubber in order to improve the mechanical properties, namely toughness. This process can be applied to not only pure syndiotactic PMMA, but also to a blend of syndiotactic and atactic PMMAs in order to form a stereo complex.

The polyacrylate rubber copolymer is composed of alkyl acryl ester and cross-linkable vinyl monomer. Here, the alkyl acryl ester includes acryl methyl, acryl ethyl, acryl propyl, acryl i-propyl, acryl n-butyl, acryl i-butyl, acryl t-butyl, acryl n-hexyl, acryl octyl, acryl 2-ethylhexyl, and acryl lauryl. Especially, acryl ethyl, acryl n-butyl and acryl 2-ethylhexyl are preferable because those compounds show a low Tg of −22, −54 and −85° C., and then good elasticity.

The cross-linkable vinyl monomer includes 2-chloroethyl-vinyl-ether, acrylonitrile, glycidyl-methacrylate and acryl-glycidyl-ether. The monomer is copolymerized in a range of 5 to 20% with the above alkyl acryl ester.

The alkyl acryl ester of the methylmethacrylate-alkylacrylate-styrene terpolymer includes acryl methyl, acryl ethyl, acryl propyl, acryl i-propyl, acryl n-butyl, acryl i-butyl, acryl t-butyl, acryl n-hexyl, acryl octyl, acryl 2-ethylhexyl, and acryl lauryl, the same as in the case of the copolymer.

The fluororubber includes VDF-HFP, VDF-CTFE, PTFE-P, VDF-PFVE, TFE-PFVE, FVMQ and VNF (referred to in "Plastic Encyclopedia" p. 509, Asakura).

It is possible in Me present invention to employ a wide range of mixture ratio of polar elastomer selected from a group of polyacrylate rubber copolymer, methylmethacrylate-alkylacrylate-styrene terpolymer, and fluororubber, and PMMA. A preferable weight ratio of the elastomer to the PMMA is a range of 2 to 30 wt. %, and a more preferable ratio is a range of 5 to 15 wt. %. This is because a denture having a mixture ratio of less than 2 wt. % or more than 30 wt. % shows relatively poor toughness or obstruction to PMMA properties.

The invented denture fabricated of injectable PMMA is given a tone of similar color to capillary and molds in oral mucous membrane, by adding red, brown or yellowish white dyes, pigment or dyed fibers. Furthermore, it is possible to optionally add inorganic fillers such as calcium oxide, titanium oxide or hydroxyapatite. The dyed fiber includes natural, chemical or synthetic fibers having heat-resistant properties, in which the fibers are preferable to show heat stability at injection temperatures in a range of 200 to 270 ° C., easy dyeability and adhesion with PMMA. It is possible to choose cotton, rayon, polyacrylonitrile, nylon 66, polyimide and PVA as the above fiber.

The denture fabricated by injecting PMMA pellets cohered with red dyed fiber, looks like a tone of similar color to capillary and molds in oral mucous membrane, because red dyed fiber uniformly disperses throughout the molded denture.

A preferable mixture ratio of the red dyed fiber to the PMMA pellet is a range of 0.01 to 10 wt. %, and a more preferable ratio is a range of 0.1 to 0.5 wt. %. Because a denture having a mixture ratio of less than 0.01 wt. % or more than 10 wt. % shows insufficient coloring or obstruction to PMMA properties. A preferable diameter and length of the fiber is a range of 1 to 30 μm and 0.5 to 3 mm, and the injected denture fabricated of the above fiber looks like a tone of similar appearance to capillary and molds in oral mucous membrane, because of uniformly dispersing and maintaining the fiber shape after injection.

A method for producing the tough denture, is composed of following steps:

step 1: polymerizing the polymethyl-methacrylate;

step 2: mixing polar elastomer selected from a group of polyacrylate rubber copolymer, methylmethacrylate-alkylacrylate-styrene terpolymer, and fluororubber into the polymethylmethacrylate and pelletizing the mixture;

step 3: optionally adding red, brown or yellowish white dyes, pigment or dyed fibers, furthermore, optionally adding inorganic fillers such as calcium oxide, titanium oxide or hydroxyapatite;

step 4: purifying the gained pellet;

step 5: drying the pellet in a range of 60 to 120° C. more than 4 hours in order to reduce moisture content to less than 2%; and step 6: injecting the dried pellet to form a denture shape in denture mold in a range of 220 to 270° C.

A method of producing PMMA is possibly employed with the ordinary method, for example, disclosed in Jpn 5/139925. The denture is usually produced according to above described steps of 2 to 5, but in step 6 of injection, in order to prevent deterioration of PMMA and fiber an injection temperature of more than 270° C. is avoided.

A PMMA denture of the present invention is possibly given an antibacterial property by adding inorganic antibacterial agent.

In conclusion, a PMMA denture of the present invention shows improved safety to living organisms and increased productivity of molding because of excellent mechanical properties and remarkable elution volume decrease after polymerization in comparison with ordinary type dentures of heat-polymerized PMMA. Furthermore, it is possible to widely apply the denture in clinical use because of good adaptability in oral applications with economical advantages.

EXAMPLE

Details of the present invention are explained by the following examples.

Mechanical properties and eluted volume of dissolved monomer residue after injection molded castings, of examples 1 to 7 and comparative examples 1 and 2 are measured according to ASTM and weight decrease of the castings after dipping and stirring 3 days at 50° C. in methanol.

Table 1 and 3 show tensile strength, Izod impact strength and bending strain. And table 2 and 4 show the elated volume according to above described method.

Example 1

The syndiotactic and atactic PMMA pellets having weight-average molecular weights of about 220 and 280 thousand are mixed with each other in a ratio of 50 by 50 wt. %, molded in plaster mold by injector, and fabricated castings.

Example 2

Copolymer blend composed of syndiotactic PMMA of 90 wt. % having weight-average molecular weight of 120 thousand and n-butyl acrylate of 10 wt. % are made into pellets, molded in plaster mold by injector, and fabricated castings.

Example 3

Syndiotactic PMMA pellets having weight-average molecular weight of 120 thousand, are cohered by red dyed cellulose fiber of 0.2 wt. %, molded in plaster mold by injector, and fabricated castings.

Comparative Example 1

Methylmethacrylate of 50 wt. % is mixed with PMMA powder of 50 wt. % having weight-average molecular weight of 460 thousand, made into a paste, molded in plaster mold, and fabricated castings.

TABLE 1

| Specimen Test Item | Example 1 | Example 2 | Example 3 | Comparative Example 1 |
|---|---|---|---|---|
| Tensile Strength at Break (MPa) | 82.3 | 77.8 | 76.4 | 74.6 |
| Bending | | | | |
| 3.5 kgf Strain (mm) | 1.50 | 1.56 | 1.58 | 1.85 |
| 5.0 kgf | 2.53 | 2.64 | 2.75 | 3.53 |
| Izod Impact Strength kg · cm/cm$^2$ | 1.75 | 1.68 | 1.62 | 1.54 |

TABLE 2

| Specimen | eluted volume (%)* |
|---|---|
| Example 1 | 1.96 ± 0.64 |
| Example 2 | 1.78 ± 0.72 |
| Example 3 | 1.82 ± 0.60 |
| Comparative Example 1 | 8.05 ± 0.96 |

*average ± standard variation n = 3

Example 4

Copolymer blend composed of syndiotactic PMMA of 90 wt. % having weight-average molecular weight of 120 thousand and n-butyl acrylate of 10 wt. %, is cohered by legal pigment of Brown No. 201 (fabricated by Kiki Kasei Ltd.) in a ratio of 0.1 parts to 100 parts of the polymer, molded in plaster mold by injector, and fabricated castings.

Example 5

Copolymer blend composed of syndiotactic PMMA of 90 wt. % having weight-average molecular weight of 120 thousand and n-butyl acrylate of 10 wt. %, is cohered by legal pigment of Yellow No. 205 (fabricated by Kiki Kasei Ltd.) in a ratio of 0.1 parts to 100 parts of the polymer, molded in plaster mold by injector, and fabricated castings.

Example 6

Copolymer blend composed of syndiotactic PMMA of 90 wt. % having weight-average molecular weight of 120 thousand and n-butyl acrylate of 10 wt. %, is cohere by a mixture composed of 100 pats of the polymer, 0.1 parts of above mentioned Brown pigment No. 201 and 0.4 parts of tribasic calcium phosphate (Wako Ltd.), molded in plaster mold by injector, and fabricated castings.

Example 7

Copolymer blend composed of syndiotactic PMMA of 90 wt. % having weight-average molecular weight of 120 thousand and n-butyl acrylate of 10 wt. %, is cohered by a mixture composed of 100 parts of the polymer, 0.1 parts of above mentioned Yellow pigment No. 201 and 0.3 parts of Anatase form titanium dioxide (Wako Ltd.), molded in plaster mold by injector, and fabricated castings.

Comparative Example 2

Copolymer blend composed of syndiotactic PMMA of 99.9 wt. % having weight-average molecular weight of 120 thousand and n-butyl acrylate of 0.1 wt. % is made into pellets, molded in plaster mold by injector, and fabricated castings.

TABLE 3

| Specimen Test Item | Example 4 | Example 5 | Example 6 | Example 7 | Comparative Example 2 |
|---|---|---|---|---|---|
| Tensile Strength at Break (MPa) Bending | 76.5 | 76.6 | 75.7 | 75.3 | 74.7 |
| 3.5 kgf Strain (mm) | 1.51 | 1.57 | 1.57 | 1.48 | 1.84 |
| 5.0 kgf | 2.66 | 2.70 | 2.75 | 2.68 | 3.51 |
| Izod Impact Strength kg · cm/cm$^2$ | 1.79 | 1.75 | 1.69 | 1.71 | 1.56 |

TABLE 4

| Specimen | eluted volume (%)* |
|---|---|
| Example 4 | 1.80 ± 0.52 |
| Example 5 | 1.90 ± 0.77 |
| Example 6 | 1.78 ± 0.74 |
| Example 7 | 1.81 ± 0.63 |
| Comparative Example 2 | 1.82 ± 0.74 |

*average ± standard variation n = 3

What we claim is:

1. A tough denture which comprises a mixture of solid polymethyl-methacrylate as a main component and a polar elastomer selected from the group consisting of polyacrylate rubber copolymer of an alkyl acrylate and a cross-linkable vinyl monomer, methylmethacrylate-alkylacrylate-styrene terpolymer, and fluororubber, said denture having been fabricated by a process of the components being mixed and injected into a denture mold.

2. The tough denture of claim 1, in which the polymethyl-methacrylate includes a stereo complex comprsing a blend of syndiotactic and atactic polymethyl-methacrylates.

3. The tough denture of claim 1, in which a weight-average molecular weight of the polymethyl-methacrylate is in a range of 100,000 to 300,000.

4. The tough denture of claim 1, in which the polyacrylate rubber is composed of (a) a copolymer of any one of ethylacrylate, butylacrylate, and 2-ethylacrylate and (b) cross-linkable vinyl monomer.

5. The tough denture of claim 1, further comprising red dyed fibers mixed with the polymethyl-methacrylate.

6. A method for producing a tough denture, comprising the steps of:

(a) mixing polar elastomer selected from the group consisting of polyacrylate rubber copolymer of an alkylacrylate and a cross-linkable vinyl monomer, methylmethacrylate-alkylacrylate-styrene terpolymer, and fluororubber with polymethyl-methacrylate having a weight average molecular weight of 100,000 to 300,000, and pelleting, (b) optionally mixing red-dyed fibers with the pellets (c) purifying the pellets, (d) drying the pellets in a range of 60 to 120° C. for more than 4 hours in order to reduce moisture content to less than 2%, and (e) melting the dried pellets in a range of 220 to 270° C. and injection molding the resultant melt in a denture mold to form the denture.

7. The method for producing a tough denture according to claim 6, comprising the additional step of mixing the polymethyl-methacrylate with red dyed fibers before step (a).

8. The method for producing a tough denture according to claim 6, wherein the polymethyl-methacrylate includes a stereo complex comprising a blend of syndiotactic and atactic polymethyl-methacrylates.

9. The method for producing a tough denture according to claim 6, wherein the polyacrylate rubber is composed of (a) a co-polymer of any one of ethylacrylate, butylacrylate, and 2-ethylacrylate and (b) cross-linkable vinyl monomer.

* * * * *